United States Patent
Meegan et al.

(10) Patent No.: US 11,685,707 B2
(45) Date of Patent: Jun. 27, 2023

(54) METHOD FOR MAKING A DI(AMINOARYL)FLUORENE COMPOUND

(71) Applicant: Cytec Industries Inc., Princeton, NJ (US)

(72) Inventors: Jonathan E. Meegan, Chester (GB); Victor Maruani, Lyons (FR); Vincent Schanen, Lyons (FR); Paul Cross, York (GB)

( * ) Notice: Subject to any disclaimer, the term of this patent is extended or adjusted under 35 U.S.C. 154(b) by 0 days.

(21) Appl. No.: 17/415,378

(22) PCT Filed: Dec. 20, 2019

(86) PCT No.: PCT/US2019/067775
§ 371 (c)(1),
(2) Date: Jun. 17, 2021

(87) PCT Pub. No.: WO2020/132406
PCT Pub. Date: Jun. 25, 2020

(65) Prior Publication Data
US 2022/0064099 A1 Mar. 3, 2022

Related U.S. Application Data

(60) Provisional application No. 62/782,711, filed on Dec. 20, 2018.

(51) Int. Cl.
*C07C 209/84* (2006.01)

(52) U.S. Cl.
CPC .................. *C07C 209/84* (2013.01)

(58) Field of Classification Search
CPC ... C07C 209/84; C07C 209/60; C07C 209/78; C07C 211/55; C07C 211/54
See application file for complete search history.

(56) References Cited

U.S. PATENT DOCUMENTS

| | | | | |
|---|---|---|---|---|
| 4,684,678 A * | 8/1987 | Schultz | ................ | C08G 59/245 523/466 |
| 6,887,973 B2 * | 5/2005 | Towns | .................. | C08G 61/02 428/917 |
| 7,863,347 B2 * | 1/2011 | Fujita | ................ | H01L 21/02282 528/307 |
| 10,011,679 B2 * | 7/2018 | Meegan | ................ | C07C 211/50 |
| 10,196,479 B2 * | 2/2019 | Meegan | ............. | C08G 59/5033 |
| 2009/0278442 A1 * | 11/2009 | Miki | .................. | H01L 51/0059 564/309 |
| 2016/0152763 A1 * | 6/2016 | Meegan | .................. | C08K 5/18 252/182.13 |

(Continued)

FOREIGN PATENT DOCUMENTS

CN 101643381 A 2/2010
CN 104926667 A * 9/2015

(Continued)

OTHER PUBLICATIONS

A. Butrow et al., 54 Journal of Chemical & Engineering Data, 1876-1883 (2009) (Year: 2009).*
Hawley's Condensed Chemical Dictionary, p. 1276-1277 (16th ed., 2016, R.J. Larrañaga ed.) (Year: 2016).*
ThermoFisher Scientific, Safety Data Sheet for Methanesulfonic acid, (2010) (Year: 2010).*
ThermoFisher Scientific, Safety Data Sheet for Sulfuric acid, (2010) (Year: 2010).*
N. G. Anderson, Practical Process & Research Development (2000) (Year: 2000).*

(Continued)

*Primary Examiner* — Alexander R Pagano
(74) *Attorney, Agent, or Firm* — Thi Dang

(57) ABSTRACT

The present invention is directed to a method for making a di(aminoaryl)fluorene compound that includes the steps of: (a) reacting a fluorenone compound according structure (I) with excess aminobenzene according to structure (II) wherein: each $R^1$, $R^2$, $R^3$, $R^4$, $R^{12}$, and $R^{13}$ is independently a group that is inert in the polymerization of epoxy compounds, and $R^{11}$ is H or $(C_1-C_6)$alkyl, in the presence of an acid catalyst, in a liquid medium comprising an aromatic or substituted aromatic solvent having a boiling point of greater than or equal to 150° C. and in the presence of an acid catalyst, in a liquid medium comprising an aromatic or substituted aromatic solvent having a boiling point of greater than or equal to 150° C. and from which the di(aminoaryl) fluorene compound is crystallizable, to form a crude product mixture comprising the di(aminoaryl)fluorene compound, (b) crystallizing di(aminoaryl)fluorene compound in the product mixture, and (c) separating the product mixture into crystallized di(aminoaryl)fluorene compound and a filtrate.

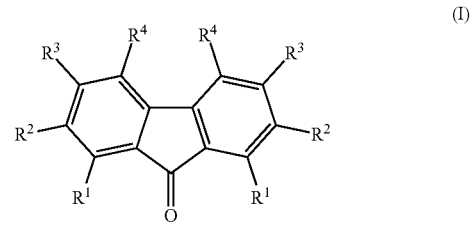

(I)

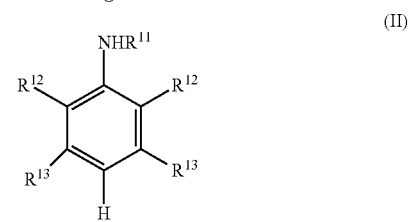

(II)

21 Claims, No Drawings

(56) References Cited

U.S. PATENT DOCUMENTS

2021/0130540 A1* 5/2021 Zucchi ................ G01N 27/127

FOREIGN PATENT DOCUMENTS

| CN | 104926667 A | 9/2015 |
| EP | 0418939 B1 | 11/1993 |
| EP | 08021717 B1 | 7/1999 |
| JP | 2011084502 A | 4/2011 |
| SU | 1664787 A1 | 7/1991 |

OTHER PUBLICATIONS

J. Guo et al., 3 Green Chemistry, 193-195 (2001) (Year: 2001).*
C. Meng et al., 121 Reac. Kinet. Mech. Cat., 719-734 (2017) (Year: 2017).*
N. G. Anderson, Practical Process & Research Development, Chapter 11, pp. 223-247 (2000) (Year: 2000).*

* cited by examiner

METHOD FOR MAKING A DI(AMINOARYL)FLUORENE COMPOUND

The instant application is a U.S. national phase entry under 35 U.S.C. § 371 of International Application No. PCT/US2019/067775 filed on Dec. 20, 2019, which claims the benefit of prior U.S. Provisional Application No. 62/782,711 filed on Dec. 20, 2018, the content of each of these applications is incorporated herein by reference in its entirety.

FIELD OF THE INVENTION

This invention relates to a method for making a di(aminoaryl)fluorene compound.

BACKGROUND OF THE INVENTION

Certain 9,9-bis(aminophenyl)fluorene compounds, such as 9,9-bis(3,5-dichloro-4-aminophenol)fluorene compound ("CAF"), are known to be useful as curing agents for epoxy resins (see, for example, U.S. Pat. No. 4,684,678).

Synthesis of high purity CAF can generate a large amount of waste. For example, in the CAF synthesis method described in U.S. Pat. No. 4,684,678 is conducted in a large excess of 2-chloroaniline, the reaction product is precipitated in methanol and then washed in methanol. Handling the large excess volume of 2-chloroaniline, which is difficult to recycle, and large volume of waste methanol wash liquid add cost to the process.

SUMMARY OF THE INVENTION

The present invention is directed to a method for making a di(aminoaryl)fluorene compound, comprising:
(a) reacting a fluorenone compound according structure (I):

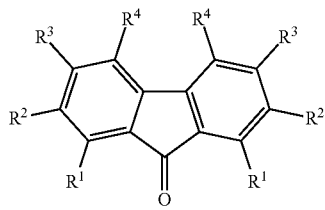

with excess aminobenzene according to structure (II):

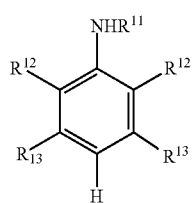

wherein:
each $R^1$, $R^2$, $R^3$, $R^4$, $R^{12}$, and $R^{13}$ is independently a group that is inert in the polymerization of epoxy compounds, and
$R^{11}$ is H or $(C_1-C_5)$alkyl, in the presence of an acid catalyst, in a liquid medium comprising an aromatic or substituted aromatic solvent having a boiling point of greater than or equal to 150° C. and from which the di(aminoaryl)fluorene compound is crystallizable, to form a crude product mixture comprising the di(aminoaryl)fluorene compound,
(b) crystallizing di(aminoaryl)fluorene compound in the product mixture, and
(c) separating the product mixture into crystallized di(aminoaryl)fluorene compound and a filtrate.

In one embodiment, the di(aminoaryl)fluorene compound is 9,9-bis(3,5-dichloro-4-aminophenol)fluorene.

DETAILED DESCRIPTION OF INVENTION AND PREFERRED EMBODIMENTS

As used herein, the term "alkoxy" means a saturated straight or branched alkyl ether radical, more typically a $(C_1-C_{22})$ alkyl ether radical, such as, for example, methoxy, ethoxy, n-propoxy, isopropoxy, n-butoxy, tert-butoxy, sec-butoxy, n-pentoxy, or nonoxy.

As used herein, the term "alkyl" means a monovalent straight or branched saturated hydrocarbon radical, more typically, a monovalent straight or branched saturated $(C_1-C_{22})$ hydrocarbon radical, such as, for example, methyl, ethyl, n-propyl, isopropyl, n-butyl, isobutyl, tert-butyl, n-hexyl, n-octyl, or n-hexadecyl.

As used herein in reference to an organic compound, the term "aromatic" means that the organic compound that comprises one or more one aryl moieties, which may each optionally be interrupted by one or more heteroatoms, typically selected from oxygen, nitrogen, and sulfur heteroatoms, and one or more of the carbon atoms of one or more one aryl moieties may optionally be substituted with one or more organic groups such as, for example, alkyl, alkoxyl, hydroxyalkyl, cycloalkyl, alkoxyalkyl, haloalkyl, aryl, alkaryl, or aralkyl.

As used herein, the term "aryl" means cyclic, coplanar 5- or 6-membered organic group having a delocalized, conjugated π system, with a number of π electrons that is equal to 4n+2, where n is 0 or a positive integer, including compounds where each of the ring members is a carbon atom, such as benzene, compounds where one or more of the ring members is a heteroatom, typically selected from oxygen, nitrogen and sulfur atoms, such as furan, pyridine, imidazole, and thiophene, and wherein one or more of the ring carbons may be substituted with one or more organic groups.

As used herein, the terminology "$(CO_n-C_m)$" in reference to an organic group, wherein n and m are each integers, indicates that the group may contain from n carbon atoms to m carbon atoms per group.

The terms "cure" and "curing" as used herein may include polymerizing and/or cross-linking of the curable resin composition.

As used herein, the term "curing agent" means a compound or complex that is capable of dissociating to provide one or more species capable of initiating polymerization of the curable resin component of the curable resin composition of the present invention.

As used herein, the term "cycloalkyl" means a saturated $(C_5-C_{22})$ hydrocarbon radical that includes one or more cyclic alkyl rings, such as, for example, cyclopentyl, cyclooctyl, or adamantanyl.

As used herein, "epoxide group" means a vicinal epoxy group, that is, a 1,2-epoxy group.

As used herein, the term "halo" means a halogen radical, that is, a chloro, fluoro, bromo, or iodo group.

Groups that are inert in the polymerization and are suitable as $R^1$, $R^2$, $R^3$, and $R^4$ of the fluorenone compound according structure (I) and $R^{12}$ and $R^{13}$ of the aminobenzene according to structure (II) include: H, alkyl, alkoxyl, cycloalkyl, and monocylic aryl, which may optionally be substituted on one or more carbon atoms of the aryl ring with alkyl. More typically, each $R^1$, $R^2$, $R^3$, and $R^4$ of the fluorenone compound according structure (I) and $R^{12}$ and $R^{13}$ of the aminobenzene according to structure (II) is independently H, $(C_1-C_6)$alkyl, $(C_1-C_6)$alkoxyl, cyclohexyl, or phenyl.

In one embodiment, each $R^1$, $R^2$, $R^3$, and $R^4$ is independently H or $(C_1-C_6)$alkyl.

In one embodiment, each $R^1$, $R^2$, $R^3$, and $R^4$ is H.

Suitable fluorenone compounds include fluorenone,
1,2-dihydroxyfluoren-9-one,
3,4-dihydroxyfluoren-9-one,
1,2,6,7-tetrahydroxyfluoren-9-one,
1,2-diamino-fluoren-9-one,
(R)-1,11-carbonylaporphine,
7(h)-oxo-1,2,3,4,5,6-hexahyrdobicyclopentafluorene,
13(h)-oxo-1,2,3,4,5,6,7,8-octahyrdobicyclohexafluorene,
1,2,3,4-tetrahydro-11-methoxy-13H-dibenzo[a,g]fluoren-13-one,
11-acetyloxy-1,2,3,4-tetrahydro-13H-dibenzo[a,g]fluoren-13-one, and
5-phenyl-5,10-dihydrobenzo[b]fluoren-11-one.

In one embodiment, the fluorenone compound comprises fluorenone.

In one embodiment, $R^{11}$ is H or $(C_1-C_6)$alkyl, and each $R^{12}$ and $R^{13}$ is independently H, $(C_1-C_6)$alkyl, nitro, hydroxyl, or halo.

In one embodiment, $R^{11}$ is H and each $R^{12}$ and $R^{13}$ is independently H, $(C_1-C_6)$alkyl, nitro, hydroxyl, or halo, provided that at least one $R^{12}$ or $R^{13}$ is halo.

In one embodiment, $R^{11}$ is H, one $R^{12}$ is halo, more typically chloro, the other $R^{12}$ is H, and each $R^{13}$ is H.

Suitable aminobenzenes include 2-chloroaniline, 2-bromoaniline, 2-fluoroaniline, 2-iodoaniline, 2,6-dichloroaniline, 2,6-dibromoaniline, 2,6-difluoroaniline, 2,6-diiodoaniline, 2,6-dihydroxyaniline, 2-nitroaniline, 3-nitroaniline, 2-hydroxyaniline, 3-bromoaniline, 3-fluoroaniline, 3-iodoaniline, 3,5-dichloroaniline, 3,5-dibromoaniline, 3,5-difluoroaniline, 3,5-diiodoaniline, and 3,5-dihydroxyaniline.

In one embodiment, the aminobenzene according to structure (II) is initially present in from 1 to 12, 1.5 to 10, more typically 2 to 6, times the stoichiometric amount, based on the amount of the fluorenone compound.

In one embodiment, the acid catalyst comprises a nonvolatile strong acid that is soluble in the liquid medium, selected from the group consisting of Lewis acids having a high affinity for oxygen and Brønsted acids. Suitable Lewis acids include $AlCl_3$, $YbCl_3$, $GdCl_3$, $TiCl_2$, $Al_2(SO_4)_3$, $CuSO_4$, $Yb(SO_4)_3$, and ytterbium trifluoromethane sulfonate. Suitable Brønsted acids include methane sulfonic acid, ethane sulfonic acid, 1,2-ethane disulfonic acid, propane sulfonic acid, benzene sulfonic acid, p-toluene sulfonic acid, trifluoromethane sulfonic acid, $H_2SO_4$, HCl, and $H_3PO_4$.

In one embodiment, the acid catalyst comprises a Lewis acid.

In one embodiment, the acid catalyst comprises a Brønsted acid.

In one embodiment, the acid catalyst comprises methane sulfonic acid.

The catalyst is present in a catalytically effective amount, typically from 0.01 to 0.5, more typically from 0.1 to 0.3, pbw catalyst per 1 pbw the fluorenone compound according structure (I).

In one embodiment, the solvent in which the reaction is conducted comprises an aromatic or substituted aromatic solvent:
(i) having a boiling point of greater than or equal to 150° C.,
(ii) that is non-reactive with any of the other components of the reaction or product mixtures, including the fluorenone compound, the aminobenzene, and the di(aminoaryl)fluorene compound,
(iii) in which the fluorenone compound according to structure (I) and the aminobenzene according to structure (II) are each soluble, and
(iv) from which the di(aminoaryl)fluorene compound is crystallizable.

In one embodiment, the solvent in which the reaction is conducted is a solvent in which the fluorenone compound according to structure (I) and the aminobenzene according to structure (II) are each soluble at or near the boiling point of the solvent as well as at reduced temperature, such as at room temperature or at a temperature in the range of from 5° C. to 30° C.

As referred to herein, an indication that a crystalline compound is "crystallizable from" a solvent means that the compound can be dissolved in the solvent at an elevated temperature and can be precipitated from the solvent in crystalline solid form by reducing the temperature of a solution of the compound in the solvent, such as wherein the compound is soluble in the solvent at near or the boiling point of the solvent and is not soluble or is only slightly soluble in the solvent at reduced temperature, such as a temperature in the range of from 5° C. to 30° C.

As referred to herein, the terminology "at or near the boiling point of the solvent" means at temperatures in the range of from 25° C. less than the boiling point of the solvent to the boiling point of the solvent or from 15° C. less than the boiling point of the solvent to the boiling point of the solvent or from 10° C. less than the boiling point of the solvent to the boiling point of the solvent.

In one embodiment, the solvent comprises benzene, toluene, orthodichlorobenzene, xylene, napthalene, tristyrylphenol, or a mixture thereof.

In one embodiment, the solvent comprises ortho-dichlorobenzene.

In one embodiment the reaction mixture comprises from 2 to 10, more typically 2 to 8, parts by weight ("pbw") of the solvent per 1 pbw of the fluorenone compound according structure (I) initially present in the reaction mixture.

In one embodiment the reaction mixture initially comprises, per 100 pbw reaction mixture:
from 2 to 22, more typically from 9 to 15, pbw of the fluorenone compound according structure (I),
from 10 to 80, more typically from 40 to 65, pbw of the aminobenzene according structure (II),
from 0.5 to 8, more typically from 3 to 6, pbw of the catalyst, and
from 6 to 60, more typically from 30 to 45, pbw of the solvent.

The method of the present invention may be conducted as batch process or as a continuous process.

The fluorenone compound according structure (1), aminobenzene, catalyst, and solvent are introduced into a reaction vessel. In one embodiment, the reaction vessel comprises a continuously stirred tank reactor (a "CSTR"). Optionally, more than one CSTR may be used in series In one embodiment, the reaction mixture comprising the fluorenone compound according structure (1), aminobenzene, catalyst, and solvent is sparged while being stirred in the reaction vessel with an inert gas, typically nitrogen gas, for a time period, such as, for example, from 10 minutes to 2 hours, that is sufficient to reduce the amount of oxygen dissolved in the reaction mixture to no more than a negligible amount.

The reaction mixture comprising the fluorenone compound according structure (1), aminobenzene, catalyst, and solvent is heated to a temperature of from 140° C. to the boiling point of the solvent, typically from a temperature of from 10° C. less than the boiling point of the solvent up to, but not including, the boiling point of the solvent and maintained at a temperature within that range for a time period, such as, for example, from 1 hour to 20 hours, that is sufficient to run the reaction of the fluorenone compound according structure (1) and aminobenzene to the desired degree of completion.

The reaction of the fluorenone compound according structure (1) with the aminobenzene according structure (II) in the solvent and in the presence of the catalyst produces a crude product mixture comprising di(aminoaryl)fluorene compound, solvent, unreacted aminobenzene, unreacted fluorenone compound according structure (1), and acid catalyst.

Water is produced as a by-product of the reaction of the fluorenone compound according structure (1) with the aminobenzene according structure (II). In one embodiment, the water by-product of the reaction is continuously removed from the reaction vessel during the reaction.

In one embodiment, once the reaction has reached the desired degree of completion, the product mixture is cooled, typically to a temperature of less than or equal to 100° C., and a quantity of crystalline di(aminoaryl)fluorene compound, typically from 0.05 to 0.5 pbw of crystalline di(aminoaryl)fluorene compound per 1000 pbw of the fluorenone compound according structure (I) initially present in the reaction mixture, is added to the product mixture to seed crystallization of the di(aminoaryl)fluorene compound reaction product.

The di(aminoaryl)fluorene compound is crystallized in the product mixture by cooling the product mixture to a sufficiently low temperature, typically a temperature of from $-10°$ C. to 0° C., more typically from $-10°$ C. to 25° C., even more typically from 0° C. to 25° C., and still more typically from 0° C. to 15° C., for a sufficient period of time, typically for from 10 minutes to 10 hours, to achieve such crystallization.

In one embodiment, step (b) of the method of the present invention comprises crystallizing di(aminoaryl)fluorene compound in and directly, that is, without any intervening steps, from the product mixture formed in step (a) of the method by:
(b)(1) adding a quantity of di(aminoaryl)fluorene compound in crystalline form, typically from 0.05 to 0.5 pbw of the crystalline di(aminoaryl)fluorene compound per 1000 pbw of the fluorenone compound according structure (I) initially present in the reaction mixture, to seed crystallization of the di(aminoaryl)fluorene compound, and
(b)(2) cooling the product mixture, typically to a temperature of from $-10°$ C. to 25° C., more typically from 0° C. to 25° C., even more typically from 0° C. to 15° C., for a sufficient period of time, typically for from 10 minutes to 10 hours, to achieve such crystallization.

The crystallized di(aminoaryl)fluorene compound is then isolated from the cooled product mixture by separating the cooled product mixture into crystallized di(aminoaryl)fluorene compound and a product mixture filtrate. The separation may be achieved by any applicable liquid-solid separation process, such as centrifugation, sedimentation, and/or filtration, including filtration by gravity, under pressure, with compression, or under vacuum.

The product mixture filtrate comprises solvent, unreacted aminobenzene according structure (II), unreacted fluorenone compound according structure (I), some (di(aminoaryl)fluorene compound, and acid catalyst.

In one embodiment, the method of the present invention further comprises recycling the product mixture filtrate from step (c) of the method to step (a) of the method.

In one embodiment the method of the present invention, wherein the product mixture filtrate from step (c) of the method is recycled to step (a) of the method, the global yield of di(aminoaryl)fluorene compound is greater than or equal to 60%.

In one embodiment, the method further comprises washing the di(aminoaryl)fluorene compound isolated from the product mixture with a first washing liquid that comprises an aromatic or substituted aromatic solvent.

In one embodiment, the first washing liquid comprises an aromatic or substituted aromatic solvent having a boiling point of greater than or equal to 150° C. and in which the di(aminoaryl)fluorene compound is not soluble or is only slightly soluble at room temperature.

Solvents suitable as the solvent for the reaction are also suitable as the first washing liquid. In one embodiment, the choice of reaction solvent and choice of first washing solvent is the same.

In one embodiment, the first washing liquid comprises benzene, toluene, orthodichlorobenzene, a xylene, napthalene, tristyrylphenol, or a mixture thereof.

In one embodiment, the first washing liquid comprises ortho-dichlorobenzene.

In one embodiment, the step of washing with the aromatic or substituted aromatic solvent comprises one or more, more typically one, washing step(s) wherein each such washing step comprises:
contacting the di(aminoaryl)fluorene compound isolated from the product mixture with a first washing liquid, typically with an amount of from 0.5 to 10, more typically 0.5 to 5, pbw of the first washing liquid per 1 pbw of the fluorenone compound according structure (I) initially present in the reaction mixture,
optionally, agitating the di(aminoaryl)fluorene compound in contact with the first washing liquid, and
isolating washed di(aminoaryl)fluorene compound by separating the di(aminoaryl)fluorene compound and first washing liquid into washed di(aminoaryl)fluorene compound and a first washing liquid filtrate.

In one embodiment, the method further comprises washing the washed di(aminoaryl)fluorene compound isolated from the first washing liquid filtrate with a second washing liquid comprising water, a ($C_1$-$C_4$)alkanol, or a mixture thereof. In one embodiment, the second washing liquid comprises a mixture of 10 to 90 parts by weight ($C_1$-$C_4$) alkanol and 10 to 90 parts by weight water.

In one embodiment, the step of washing with water, alkanol, or mixture thereof comprises one or more, typically from 1 to 5, washing steps, wherein each washing step comprises:
contacting the di(aminoaryl)fluorene compound isolated from the aromatic or substituted aromatic solvent wash step with a second washing liquid, typically in an amount of from 5 to 20, more typically 5 to 15, pbw of the second washing liquid per 1 pbw of fluorenone compound according structure (I) initially present in the reaction mixture, optionally, agitating the mixture of di(aminoaryl)fluorene compound in contact with the second washing liquid, and isolating washed di(aminoaryl)fluorene compound by separating the di(aminoaryl)fluorene compound and second washing liquid into washed di(aminoaryl)fluorene compound and a second washing liquid filtrate.

Following completion of washing steps, the di(aminoaryl) fluorene compound isolated from the second washing liquid filtrate of the final washing step is dried. The drying may be active, such as, for example, subjecting the di(aminoaryl) fluorene compound to elevated temperature and/or reduced pressure, and/or passive, such as, for example, allowing the di(aminoaryl)fluorene compound to dry under ambient conditions.

In one embodiment, the di(aminoaryl)fluorene compound is dried by heating the washed di(aminoaryl)fluorene compound and/or subjecting the washed di(aminoaryl)fluorene compound to reduced pressure, typically by heating to a temperature of from ambient temperature to 60° C. at a pressure of less than 200 mm Hg and maintaining such conditions for a time sufficient to reduce the amount of aromatic or substituted aromatic solvent and aqueous, alcoholic, or mixed aqueous/alcoholic washing liquid filtrate to less than or equal to a desired maximum level.

In one embodiment, the washed di(aminoaryl)fluorene compound is dried at a temperature of from 35° C. to 55° C. at a pressure of from 25 mm Hg to 100 mm Hg for a time period of from 2 to 24 hours.

In one embodiment, the method of the present invention consists essentially of:

(a) reacting a fluorenone compound according structure (I):

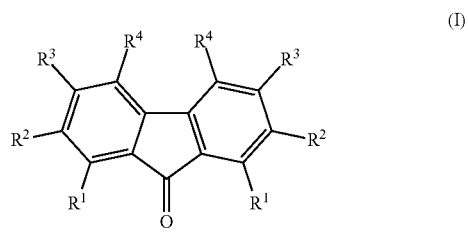

(I)

with excess aminobenzene according to structure (II):

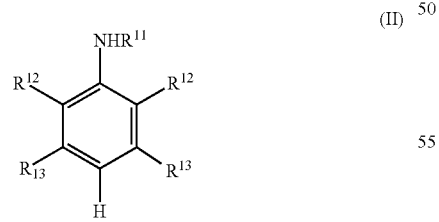

(II)

wherein:
each $R^1$, $R^2$, $R^3$, $R^4$, $R^{12}$, and $R^{13}$ is independently a group that is inert in the polymerization of epoxy compounds, and
$R^{11}$ is H or $(C_1-C_6)$alkyl, in the presence of an acid catalyst, in a liquid medium comprising an aromatic or substituted aromatic solvent having a boiling point of greater than or equal to 150° C. and from which the di(aminoaryl)fluorene compound is crystallizable, to form a crude product mixture comprising the di(aminoaryl)fluorene compound, (b) crystallizing di(aminoaryl)fluorene compound from the crude product mixture, (c) separating the product mixture into crystallized di(aminoaryl)fluorene compound and a filtrate, and, optionally, recycling at least a portion of the filtrate to step (a), (d) washing, in one or more iterations, the di(aminoaryl) fluorene compound with aromatic or substituted aromatic solvent, (e) washing, in one or more iterations, the di(aminoaryl) fluorene compound produced in step (d) with water, a $(C_1-C_4)$alkanol, or a mixture thereof, and (f) drying the di(aminoaryl)fluorene compound produced in step (e).

In one embodiment, the method of the present invention consists of the above-described steps (a), (b), (c), (d), (e), and (f).

In one embodiment, the washed di(aminoaryl)fluorene compound comprises less than 1000 parts by weight per million parts by weight ("ppm") residual acid catalyst.

In one embodiment, the washed di(aminoaryl)fluorene compound comprises less than 8000 ppm of a combined amount of residual aminobenzene and aromatic or substituted aromatic solvent.

In one embodiment, the di(aminoaryl)fluorene compound made by the method of the present invention is a compound according to structure (III):

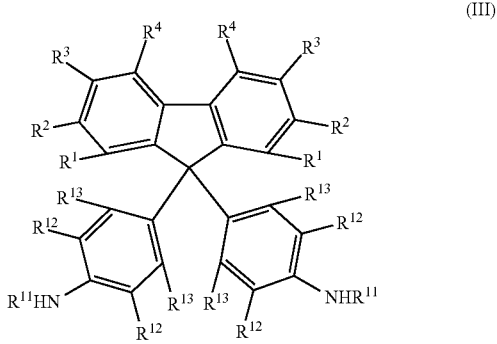

(III)

wherein $R^1$, $R^2$, $R^3$, $R^4$, $R^{11}$, $R^{12}$, and $R^{13}$ are each as described above.

In one embodiment of the di(aminoaryl)fluorene compound made by the method of the present invention:

each $R^1$, $R^2$, $R^3$, $R^4$ of the fluorenone compound according structure (I) is H, $R^{11}$, $R^{13}$ and one $R^{12}$ of the aminobenzene according to structure (II) is H, one $R^{12}$ of the aminobenzene according to structure (II) is halo, more typically chloro, and the di(aminoaryl)fluorene compound is according to structure (III.a):

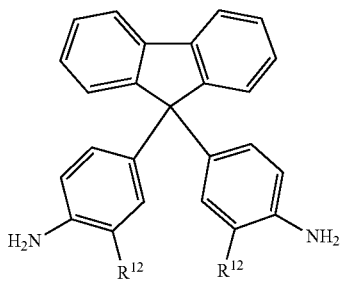

(III.a)

wherein each $R^{12}$ is halo, more typically chloro.

The method of the present invention produces a high yield of di(aminoaryl)fluorene compound having a low level of impurities and generates a reduced waste stream compared to prior art methods. In one embodiment, di(aminoaryl)fluorene compound made by the method exhibits reduced toxicity compared to di(aminoaryl)fluorene compound made by prior art methods.

EXAMPLES

In Comparative Example 1 (which is analogous to Example 4 of U.S. Pat. No. 4,684,678), fluorenone (1.000 pbw), 2-chloroaniline (7.111 pbw), methylsulfonic acid (0.267 pbw) were each charged to a continuously stirred tank reactor, sparged with $N_2$ for 0.5 hour, heated to 175° C., and then held at 175° C., while removing water formed in the reaction of the fluorenone and 2-chloroaniline, for 6.0 hours to form a crude product mixture of CAF and methyl sulfonic acid in excess 2-chloroaniline. The crude product mixture was allowed to cool and then introduced into a volume of methanol (39.600 pbw) containing 1.000 pbw trimethylamine to precipitate CAF product. The precipitated CAF was separated from the mixture by filtration and washed once with methanol (6.000 pbw) and dried.

The method of Comparative Example 1 yielded 1.702 pbw CAF and 54.977 pbw of waste, comprising 2-chloroaniline and methanol. The washed CAF comprised 240 ppm methyl sulfonic acid and 4854 ppm 2-chloraniline. The global yield of CAF was 75%.

In Example 1 of the method present invention, fluorenone (1.000 pbw), excess 2-chloroaniline (4.162 pbw), methylsulfonic acid (0.261 pbw), and in ortho-dichlorobenzene (2.650 pbw) were each charged to a continuously stirred tank reactor, sparged with $N_2$ for 0.5 hour, heated to 175° C., and then held at 175° C., while removing water formed in the reaction of the fluorenone and 2-chloroaniline, for 12.0 hours to form a crude product mixture comprising CAF, methyl sulfonic acid and 2-chloroaniline in ortho-dichlorobenzene. The crude product mixture was cooled to 85° C. and solid CAF seed crystals (0.1 pbw) were introduced to the mixture. The CAF was then recrystallized from the mixture by allowing the mixture to cool to 5° C. The crystalline CAF was separated from the cooled mixture by filtration, washed once with ortho-dichlorobenzene (1.300 pbw), and then washed three times in succession with volumes (9.000 pbw, 6.000 pbw, and 6.000 pbw, respectively) of a mixture isopropyl alcohol in water (50 pbw isopropyl alcohol/50 pbw water).

The method of Example 1 yielded 1.702 pbw CAF and 28.672 pbw of waste comprising 2-chloroaniline, ortho-dichlorobenzene, isopropyl alcohol, and water. The washed CAF comprised 75 ppm methyl sulfonic acid, 4839 ppm 2-chloraniline, and 2050 ppm ortho-diclorobenzene. The global yield of CAF was 75%.

Example 2 of the method of present invention was analogous to Example 1 of the present invention, with the added feature of recycling of ortho-dichlorobenzene. In Example 2 of the present invention, fluorenone (1.000 pbw), excess 2-chloroaniline (3.122 pbw), methylsulfonic acid (0.165 pbw), fresh ortho-dichlorobenzene (1670 pbw) and recycled filtrate, that is, a mixture comprising ortho-dichlorobenzene, 2-chloroaniline, and methyl sulfonic acid from a previous reaction (2.293 pbw) were each charged to a continuously stirred tank reactor, sparged with $N_2$ for 0.5 hour, heated to 175° C., and then held at 175° C., while removing water formed in the reaction of the fluorenone and 2-chloroaniline, for 12.0 hours to form a crude product mixture of CAF, methyl sulfonic acid, and 2-chloroaniline in ortho-dichlorobenzene. The crude product mixture was cooled to 85° C. and solid CAF seed crystals (0.1 pbw) were introduced to the mixture. The CAF was then recrystallized from the mixture by allowing the mixture to cool to 5° C. The crystalline CAF was separated from the cooled mixture by filtration, washed once with ortho-dichlorobenzene (1.300 pbw), and then washed three times in succession with volumes (9.000 pbw, 6.000 pbw, and 6.000 pbw, respectively) of a mixture isopropyl alcohol in water (50 pbw isopropyl alcohol/50 pbw water).

The method of Example 2 yielded 1.816 pbw CAF and 26.440 pbw of waste comprising 2-chloroaniline, ortho-dichlorobenzene, isopropyl alcohol, and water. The washed CAF comprised 80 ppm methyl sulfonic acid, 5295 ppm 2-chloraniline, and 2229 ppm ortho-diclorobenzene. The global yield of CAF was 80%.

The invention claimed is:
1. A method for making a di(aminoaryl)fluorene compound, comprising:
(a) reacting a fluorenone compound according structure (1):

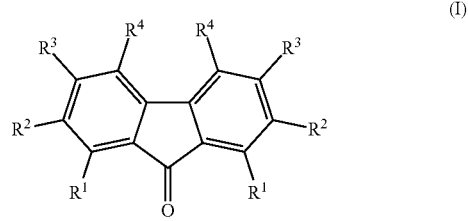

(I)

with excess aminobenzene according to structure (II):

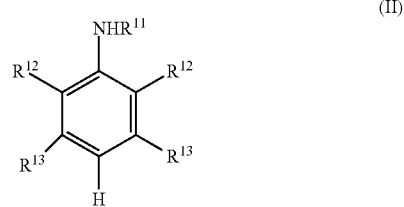

(II)

wherein:
each $R^1$, $R^2$, $R^3$, $R^4$, $R^{12}$, and $R^{13}$ is independently a group that is inert in the polymerization of epoxy compounds, and
$R^{11}$ is H or $(C_1-C_6)$alkyl,
in the presence of an acid catalyst, in a liquid medium comprising ortho-dichlorobenzene and from which the di(aminoaryl)fluorene compound is crystallizable, to form a crude product mixture comprising the di(aminoaryl)fluorene compound, wherein the acid catalyst is soluble in the liquid medium and is selected from the group consisting of: (i) Lewis acids having an affinity for oxygen, and (ii) Brønsted acids,
(b) crystallizing di(aminoaryl)fluorene compound in the crude product mixture, and
(c) separating the product mixture into crystallized di(aminoaryl)fluorene compound and a filtrate.

2. The method of claim 1, wherein each $R^1$, $R^2$, $R^3$, and $R^4$ is independently H or $(C_1-C_6)$alkyl.

3. The method of claim 1, wherein the aminobenzene is present in from 1.5 to 5 times the stoichiometric amount, based on the amount of the fluorenone compound.

4. The method of claim 1, further comprising recycling the filtrate from step (c) to step (a).

5. The method of claim 4, wherein the filtrate comprises solvent, unreacted aminobenzene, unreacted fluorenone compound according structure (1), di(aminoaryl)fluorene compound, and acid catalyst.

6. The method of claim 1, further comprising washing the di(aminoaryl)fluorene compound with additional ortho-dichlorobenzene.

7. The method of claim 6, wherein the di(aminoaryl)fluorene compound is washed with 0.5 to 100 parts by weight of ortho-dichlorobenzene per 1 pbw of the di(aminoaryl)fluorene compound.

8. The method of claim 6, further comprising washing the washed di(aminoaryl)fluorene compound with water, a $(C_1-C_4)$alkanol, or a mixture thereof.

9. The method of claim 8, wherein the di(aminoaryl)fluorene compound is washed with a mixture of 10 to 90 parts by weight $(C_1-C_4)$alkanol and 10 to 90 parts by weight water.

10. The method of claim 8, wherein the washed di(aminoaryl)fluorene compound comprises less than 1000 ppm residual acid catalyst.

11. The method of claim 8, wherein the washed di(aminoaryl)fluorene compound comprises less than 8000 ppm of a combined amount of residual aminobenzene and aromatic or substituted aromatic solvent.

12. The method of claim 1, wherein the di(aminoaryl)fluorene compound is according to structure (III):

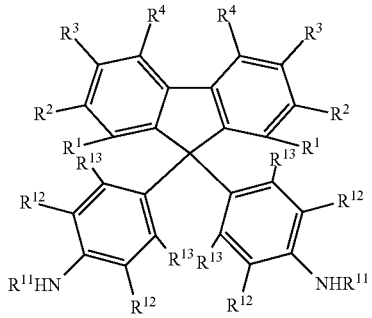

(III)

wherein:
each $R^1$, $R^2$, $R^3$, $R^4$, $R^{12}$, and $R^{13}$ is independently a group that is inert in the polymerization of epoxy compounds, and
$R^{11}$ is H or $(C_1-C_6)$alkyl.

13. The method of claim 12, wherein each $R^{12}$ is independently H or halogen, provided that at least one $R^{12}$ is halogen.

14. The method of claim 13, wherein $R^{11}$ and each $R^1$, $R^2$, $R^3$, $R^4$, and $R^{13}$ is independently H or $(C_1-C_6)$alkyl.

15. The method of claim 13, wherein $R^{11}$ and each $R^1$, $R^2$, $R^3$, $R^4$, and $R^{13}$ is H.

16. The method of claim 15, wherein the di(aminoaryl)fluorene compound is according to structure (III.a):

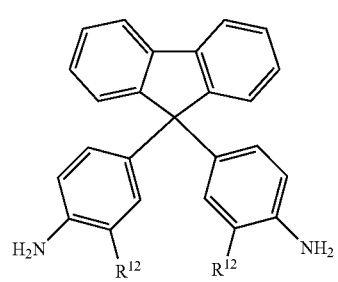

(III.a)

wherein each $R^{12}$ is halo.

17. The method of claim 16, wherein each $R^{12}$ is chloro.

18. A method for making a di(aminoaryl)fluorene compound, consisting essentially of:
(a) reacting a fluorenone compound according structure (1):

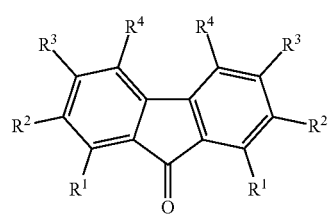

(I)

with excess aminobenzene according to structure (II):

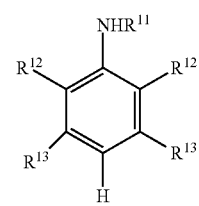

(II)

wherein:
each $R^1$, $R^2$, $R^3$, $R^4$, $R^{12}$, and $R^{13}$ is independently a group that is inert in the polymerization of epoxy compounds, and
$R^{11}$ is H or $(C_1-C_6)$alkyl,
in the presence of an acid catalyst, in a liquid medium comprising ortho-dichlorobenzene and from which the di(aminoaryl)fluorene compound is crystallizable, to form a crude product mixture comprising the di(aminoaryl)fluorene compound, wherein the acid catalyst is soluble in the liquid medium and is selected from the group consisting of: (i) Lewis acids having an affinity for oxygen, and (ii) Brønsted acids,
(b) crystallizing di(aminoaryl)fluorene compound from the crude product mixture,
(c) separating the product mixture into crystallized di(aminoaryl)fluorene compound and a filtrate, and, optionally, recycling at least a portion of the filtrate to step (a),
(d) washing, in one or more iterations, the di(aminoaryl)fluorene compound with aromatic or substituted aromatic solvent,
(e) washing, in one or more iterations, the di(aminoaryl)fluorene compound produced in step (d) with water, a $(C_1-C_4)$alkanol, or a mixture thereof, and
(f) drying the di(aminoaryl)fluorene compound produced in step (e).

19. The method of claim 18, wherein the acid catalyst is selected from: $AlCl_3$, $YbCl_3$, $GdCl_3$, $TiCl_2$, $Al_2(SO_4)_3$, $CuSO_4$, $Yb(SO_4)_3$, ytterbium trifluoromethane sulfonate, methane sulfonic acid, ethane sulfonic acid, 1,2-ethane disulfonic acid, propane sulfonic acid, benzene sulfonic acid, p-toluene sulfonic acid, trifluoromethane sulfonic acid, $H_2SO_4$, HCl, and $H_3PO_4$.

20. The method of claim 1, wherein the acid catalyst is selected from: $AlCl_3$, $YbCl_3$, $GdCl_3$, $TiCl_2$, $Al_2(SO_4)_3$, $CuSO_4$, $Yb(SO_4)_3$, ytterbium trifluoromethane sulfonate, methane sulfonic acid, ethane sulfonic acid, 1,2-ethane disulfonic acid, propane sulfonic acid, benzene sulfonic acid, p-toluene sulfonic acid, trifluoromethane sulfonic acid, $H_2SO_4$, HCl, and $H_3PO_4$.

21. The method of claim 1, wherein step (b) comprises adding a quantity of di(aminoaryl)fluorene compound in crystalline form to the crude product mixture to seed crystallization of the di(aminoaryl)fluorene compound.

* * * * *